United States Patent
Huddleston

(10) Patent No.: US 12,246,190 B1
(45) Date of Patent: *Mar. 11, 2025

(54) LASER THERAPY DEVICE AND METHOD OF CONDUCTING LASER THERAPY

(71) Applicant: JAALS, LLC, Gainesville, FL (US)

(72) Inventor: Gary A. Huddleston, Osage Beach, MO (US)

(73) Assignee: JAALS, LLC, Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/518,524

(22) Filed: Nov. 23, 2023

Related U.S. Application Data

(63) Continuation of application No. 17/839,261, filed on Jun. 13, 2022, now Pat. No. 11,878,183.

(60) Provisional application No. 63/210,202, filed on Jun. 14, 2021, provisional application No. 63/210,190, filed on Jun. 14, 2021.

(51) Int. Cl.
  *A61N 5/067* (2006.01)
  *A61N 5/06* (2006.01)

(52) U.S. Cl.
  CPC ........... *A61N 5/067* (2021.08); *A61N 5/0622* (2013.01); *A61N 2005/0632* (2013.01); *A61N 2005/0642* (2013.01)

(58) Field of Classification Search
  CPC .......................... A61N 15/067; A61N 15/0622
  USPC .......................................................... 607/89
  See application file for complete search history.

(56) References Cited

U.S. PATENT DOCUMENTS

| | | |
|---|---|---|
| 5,413,555 A | 5/1995 | McMahan |
| 5,971,978 A | 10/1999 | Mukai |
| 8,097,029 B2 | 1/2012 | Shanks et al. |
| 9,084,622 B2 | 7/2015 | Rastegar et al. |
| 9,358,402 B2 | 6/2016 | Gerlitz |
| 9,687,669 B2 | 6/2017 | Stephan |
| 9,877,361 B2 | 1/2018 | Williams |
| 9,946,082 B2 | 4/2018 | Gerlitz |
| 10,064,940 B2 | 9/2018 | Nager |
| 10,492,861 B2 | 12/2019 | Rogers |
| 10,589,119 B2 | 3/2020 | Kim et al. |
| 10,639,495 B1 | 5/2020 | Nelson et al. |
| 10,857,381 B2 | 12/2020 | Duggins |
| 10,933,253 B1 | 3/2021 | Bish et al. |
| 11,013,932 B2 | 5/2021 | Kim et al. |
| 11,878,183 B1 | 1/2024 | Huddleston |
| 2001/0008973 A1 | 7/2001 | Zuylen et al. |

(Continued)

*Primary Examiner* — Nadia A Mahmood
(74) *Attorney, Agent, or Firm* — Hanrahan Law Firm, P.A.; Benjamin M. Hanrahan

(57) ABSTRACT

A device, system and method for performing or conducting laser therapy, and more specifically, for performing Class IV laser therapy in an unattended and hands-free manner is provided herein. The system and method includes a support assembly with a laser treatment device supported thereon. The laser treatment device is configured to provide hands-free Class IV laser therapy treatment and includes a plurality of preprogrammed treatment protocols, each of the plurality of preprogrammed treatment protocols being associated with at least one of a plurality of body locations. A positionable arm extends from the support assembly and terminates at a laser emitter directed toward the selected body location. Upon selection of one of the plurality of body locations on the laser treatment device, the laser emitter will perform laser therapy treatment according to a corresponding one of the preprogrammed treatment protocols.

20 Claims, 19 Drawing Sheets

(56) References Cited

U.S. PATENT DOCUMENTS

| | | |
|---|---|---|
| 2002/0198576 A1 | 12/2002 | Chen et al. |
| 2005/0177093 A1 | 8/2005 | Barry et al. |
| 2005/0197681 A1 | 9/2005 | Barolet et al. |
| 2006/0095099 A1 | 5/2006 | Shanks et al. |
| 2009/0088822 A1 | 4/2009 | Pruitt et al. |
| 2012/0239059 A1 | 9/2012 | Jagger |
| 2014/0180368 A1 | 6/2014 | Konno |
| 2017/0215988 A1 | 8/2017 | Gregg et al. |
| 2019/0351252 A1 | 11/2019 | Taboada et al. |
| 2020/0147408 A1 | 5/2020 | Kelm et al. |
| 2021/0169573 A1 | 6/2021 | Lee |

202
204
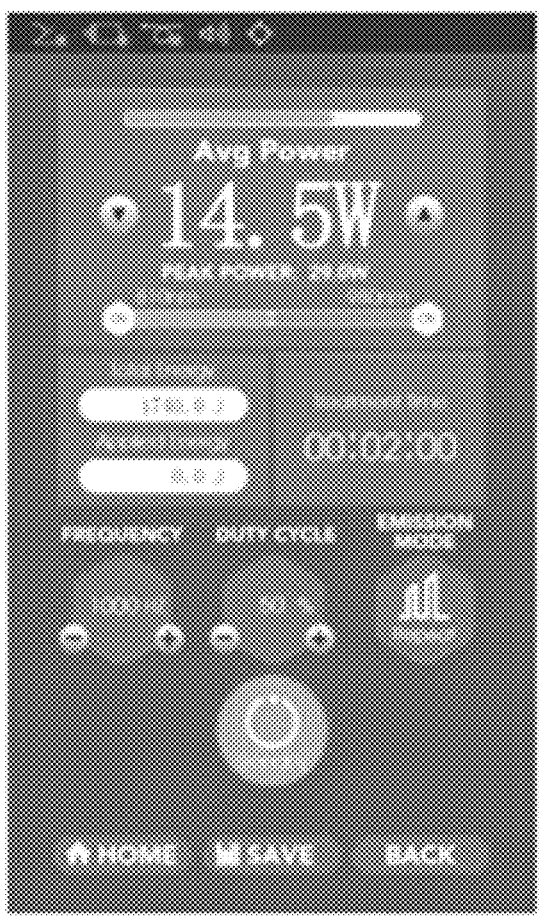
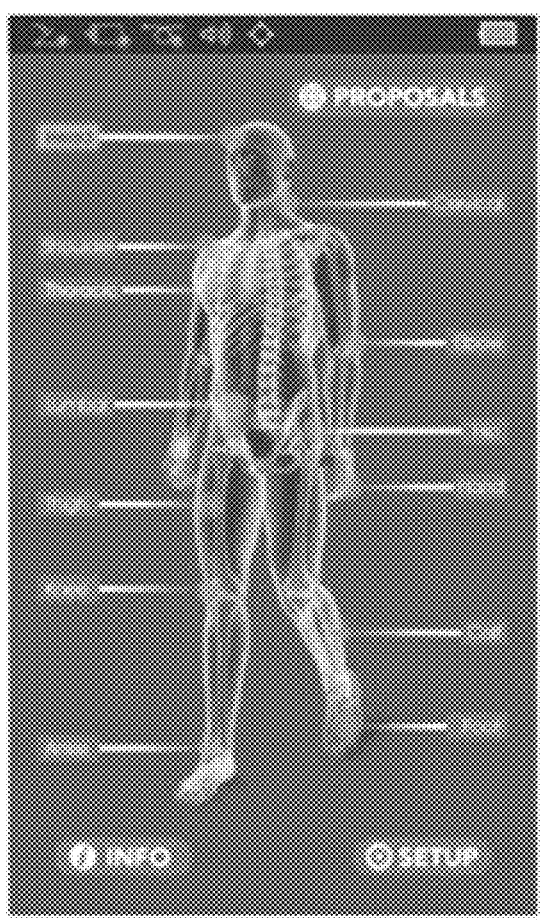
FIG. 6A
FIG. 6B

| Logic | Action | Selection | | Wavelengths | | Anatomy | Light skin CW power | light skin CW Pulsing phase time | Light-skin Pulsing avg power | Light-skin Pulsing phase time | | part size | Size | Multiplier |
|---|---|---|---|---|---|---|---|---|---|---|---|---|---|---|
| anatomy | Power and phase time settings | thoracic | | | | ankle | 6 | 25 | 6 | 30 | | m | L | 1.2 |
| acute or chronic | adjust phase time | chronic | | | | calf | 7 | 40 | 7 | 40 | | m | M | 1 |
| Part size (S,M,L) | adjusts power | L | 1.2 | | | cervical | 8 | 60 | 8 | 60 | | m | S | 0.8 |
| Skin color (light, dark) | change CW to 2Hz | dark | | | | | | | | | | | | |
| | | | | | | elbow | 5 | 40 | 6 | 30 | | m | | |
| | | | | | | foot | 5.5 | 30 | 5.5 | 30 | | m | | |
| Pain level | Adjusts power | | | | | hand | 4 | 20 | 5 | 10 | | m | Pain scale | Power multiplier |
| | | | | | | head | 4 | 40 | 4 | 30 | | m | 1 | 0.8 |
| | | | | | | hip | 10 | 70 | 9 | 45 | | m | 2 | 0.85 |
| | | | | | | jaw | 3 | 30 | 3 | 20 | | m | 3 | 0.9 |
| | | | | | | knee | 8 | 45 | 8 | 45 | | m | 4 | 0.95 |
| | | | | | | lumbar | 12 | 75 | 10 | 60 | | m | 5 | 1 |
| Phase time | Average Power Joules | | | | | sacrum | 10 | 45 | 9 | 45 | | m | 6 | 1.05 |
| 92 | 10.8 | | | 993.6 | 660, 800, 970 | shoulder | 8 | 60 | 8 | 50 | | m | 7 | 1.1 |
| 60 | 10.8 | | | 648 | 660, 800, 970 | thigh | 9 | 50 | 9 | 30 | | m | 8 | 1.15 |
| 60 | 10.8 | | | 648 | 660, 800, 970 | thoracic | 9 | 80 | 9 | 60 | | m | 9 | 1.2 |
| 60 | 10.8 | | | 648 | 660, 800, 970 | wrist | 4 | 25 | 5 | 15 | | m | 10 | 1.25 |
| 60 | 10.8 | | | 648 | 660, 800, 970 | | | | | | | | | |
| 60 | 10.8 | | | 648 | 660, 800, 970 | These are the baseline numbers for the protocols. | | | | | | | Chronicity | Multiplier |
| | | | | | | | | | | | | | acute | 1 |
| Total Time(minutes) | 8:32 | | | | | | | | | | | | chronic | 1.15 |
| Total Joules | 4233.6 | | | | | | | | | | | | | |

LASER THERAPY DEVICE AND METHOD OF CONDUCTING LASER THERAPY

CLAIM OF PRIORITY/CROSS-REFERENCE TO RELATED APPLICATION

The present application is a Continuation Patent Application of U.S. patent application Ser. No. 17/839,261 filed on Jun. 13, 2022, which is based on and claims priority under 35 U.S.C. § 119(e) to the following two provisional patent applications: U.S. Provisional Patent Application No. 63/210,190, filed on Jun. 14, 2021, and Provisional Patent Application No. 63/210,202, filed on Jun. 14, 2021.

The contents of all of the above-referenced patent applications, namely, U.S. patent application Ser. No. 17/839,261 filed on Jun. 13, 2022, U.S. Provisional Patent Application No. 63/210,190 filed on Jun. 14, 2021, and U.S. Provisional Patent Application No. 63/210,202 filed on Jun. 14, 2021 are incorporated herein in their entirety by reference.

FIELD OF THE INVENTION

The present invention is generally directed to a device, system and method for performing or conducting laser therapy, and more specifically, for performing Class IV laser therapy in an unattended and/or hands-free manner.

BACKGROUND OF THE INVENTION

Laser therapy is the non-invasive use of laser energy to generate a photochemical response in damaged or dysfunctional tissue. Laser therapy can alleviate pain, reduce inflammation and accelerate recovery from a wide range of clinical conditions. Class IV laser therapy has become the standard of care for many musculoskeletal injuries.

Laser treatment systems can optimize and promote the healing process by stimulating multiple levels of tissue regeneration mechanisms. Under the stimulation of different-wavelengths laser light, the local increase of reactive oxygen species is repaired by generating additional ATP, thereby accelerating the metabolism of the cells and repairing the biological functions of the damaged cells. During the laser therapy process, the lasers can provide a warm and soothing feeling to the patients.

Laser therapy has a number of different biological effects, such as anti-inflammation, anti-pain (analgesic), accelerated tissue repair and cell growth, improved vascular activity, increased metabolic activity, and trigger points and acupuncture points.

For instance, laser therapy has an anti-endemic effect as it causes vasodilation, but also because it activates the lymphatic drainage system (drains swollen areas). As a result, there is a reduction in swelling caused by bruising or inflammation. Laser therapy also has a high beneficial effect on nerve cells which block pain transmitted by these cells to the brain and which decreases nerve sensitivity. Also, due to less inflammation, there is less edema and less pain. Photons of light from lasers penetrate deeply into tissue and accelerate cellular reproduction and growth. The laser light increases the energy available to the cell to that the cell can take on nutrients faster and get rid of waste products. Laser light will significantly increase the formation of new capillaries in damaged tissue that speeds up the healing process, closes wounds quickly and reduces scar tissue. Furthermore, laser therapy creates higher outputs of specific enzymes, greater oxygen and food particle leads for blood cells. Laser therapy also stimulates muscle trigger points and acupuncture points on a non-invasive basis providing musculoskeletal pain relief.

Moreover, if wavelength determines a laser energy's depth of penetration, then power determines its saturation at the targeted depth. It would be a mistake to consider one without the other. Power (Watts) is the number of photons of radiation you can deliver per unit time. The energy deposited (Joules) is the accumulation of these photons over time (1 Watt=1 Joule per 1 second). By starting out with more Watts at the surface, more will penetrate to the desired depth. For example, a 1 Watt laser will take 40 seconds to deliver 10 Joules of energy to a 4 cm depth. A 4 Watt laser will take 10 seconds to deliver 10 Joules of energy to a 4 cm depth. The high-powered laser will be able to deliver therapeutic doses to deeper targets in a shorter time.

Most Class IV laser therapy is an attended therapy in that doctors must have a therapist or employee to administer the laser therapy. For instance, in some laser therapy treatment systems, doctors can choose between a pulsed treatment (e.g., with the laser being rapidly turned on/off) or a continuous wave (e.g., with the laser beam on all the time). However, when a doctor performs attended laser therapy, the doctor or other individual administering the therapy, must keep the laser emitter moving or the patient's skin will get too hot.

There is thus a need in the art for a new laser therapy device, system and/or method that will allow hands-free laser therapy treatment that completely eliminates or substantially eliminates the danger of overheating. The proposed device, system and method may use a pulsed or other program that prevents or reduces thermal overload (the skin getting too hot). Other features may include special or certain settings for different body parts or body locations that allows the laser therapy treatment to be conducted hands-fee or unattended.

SUMMARY OF THE INVENTION

The present invention is generally directed to a device, system and method for performing or conducting laser therapy, and more specifically, for performing Class IV laser therapy in an unattended and hands-free manner.

The system and method includes a support assembly with a laser treatment device supported thereon. The laser treatment device is configured to provide hands-free Class IV laser therapy treatment and includes a plurality of preprogrammed treatment protocols, each of the plurality of preprogrammed treatment protocols being associated with at least one of a plurality of body locations.

A positionable arm extends from the support assembly and terminates at a laser emitter directed toward the selected body location. Upon selection of one of the plurality of body locations on the laser treatment device, the laser emitter will perform laser therapy treatment according to a corresponding one of the preprogrammed treatment protocols.

BRIEF DESCRIPTION OF DRAWINGS

FIG. 7 illustrates an exemplary chart of various treatment settings and protocols as disclosed in accordance with at least one embodiment of the present invention.

Like reference numerals refer to like parts throughout the several views of the drawings provided herein.

DETAILED DESCRIPTION OF THE INVENTION

Figure 1A:
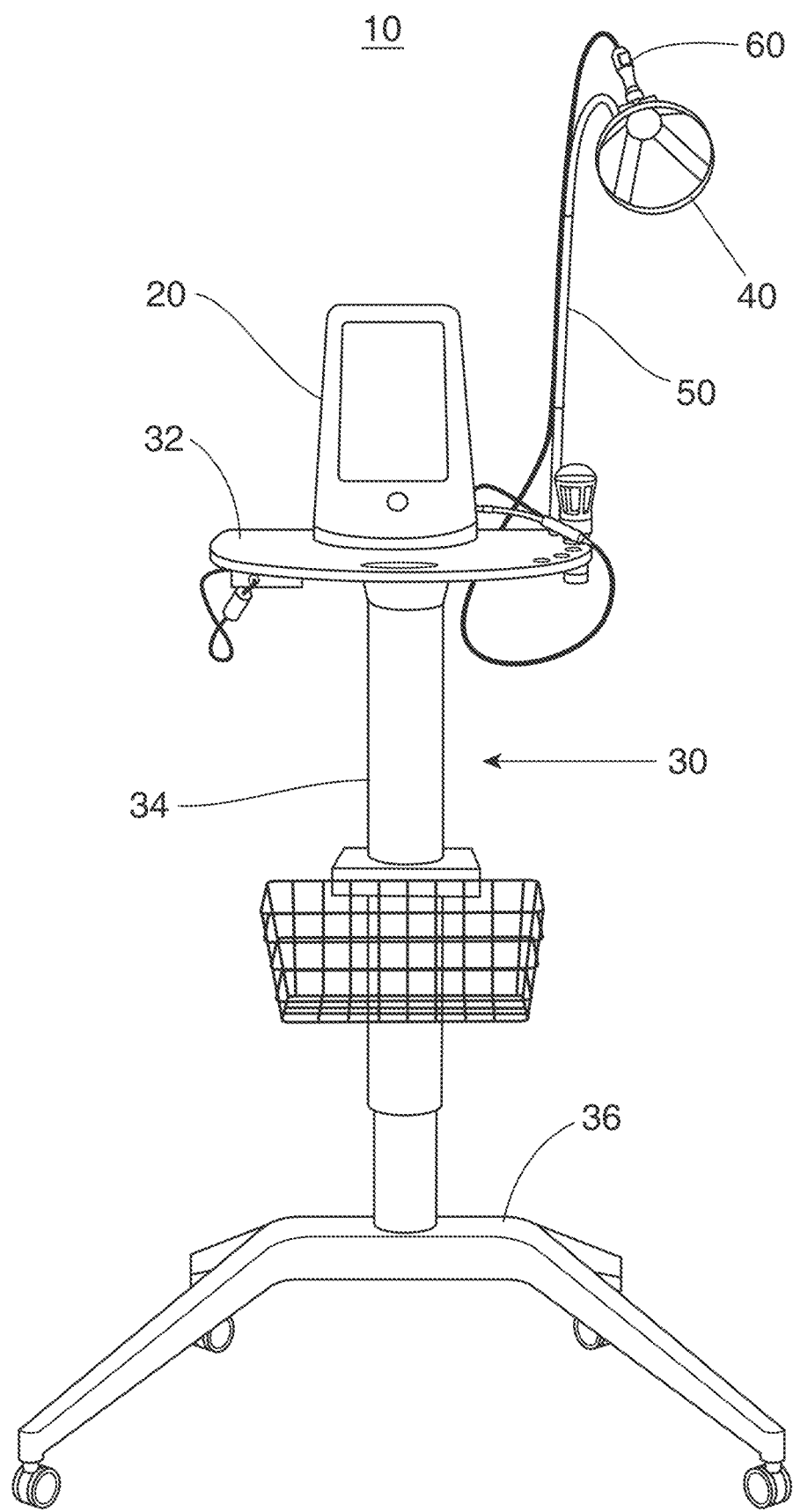
FIG. 1A is a front elevation view of the system as disclosed in accordance with at least one embodiment of the present invention.

Accordingly, as shown in the accompanying drawings, and with particular reference to FIG. 1A, the present invention is generally directed to a laser therapy device or system, represented as 10, and a method of performing laser therapy using the laser therapy device 10. In particular, diode lasers used in connection with at least one embodiment of the present invention, which can provide Class IV laser therapy, have better absorption and penetration with some of the following advantages: no pain during treatment process, effectively eliminates pain of the patients, no drug intervention, easy to perform laser therapy for doctors, non-invasive, no surgery, non-toxic FDA-approved treatment, without any known side effects, enhanced anti-inflammatory effects, and short treatment time.

Figure 1B:
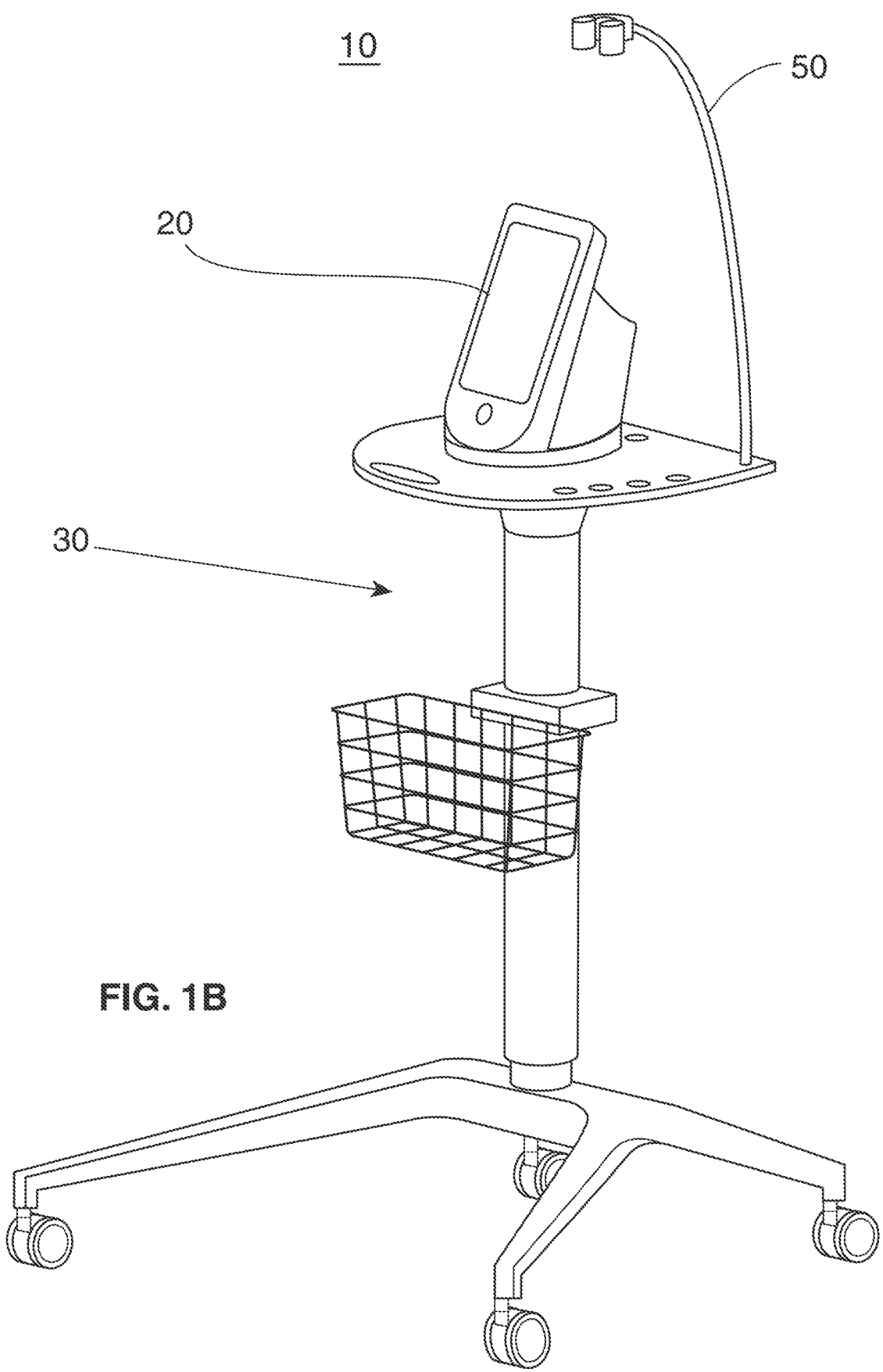
FIG. 1B is a perspective view of the system as disclosed in accordance with at least one embodiment of the present invention.
Figure 1C:
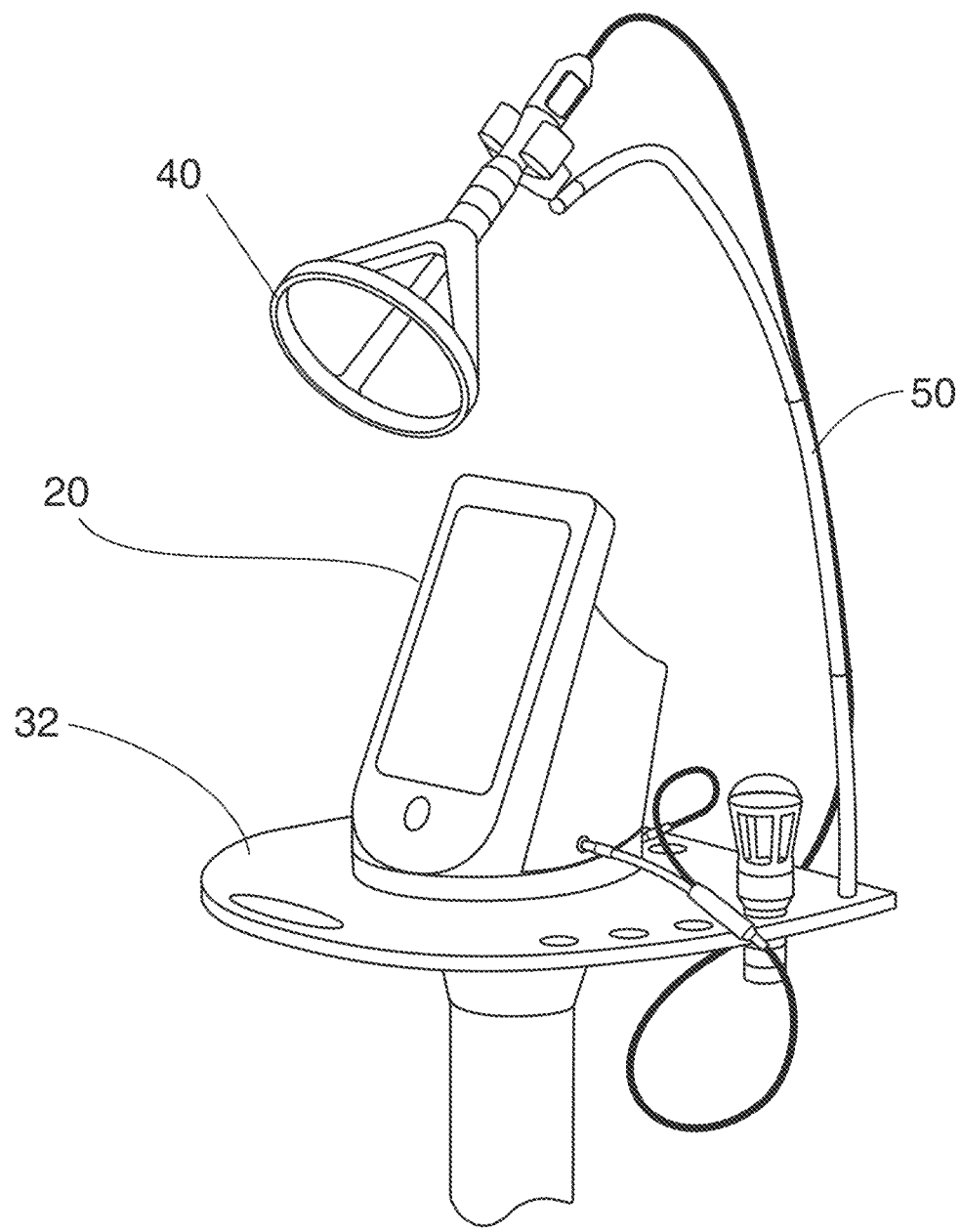
FIG. 1C is a partial perspective view of the system as disclosed in accordance with at least one embodiment of the present invention.

More specifically, as illustrated in FIGS. 1A-C, at least one embodiment of the present invention includes a laser therapy device 20, a cart or other support structure or support assembly 30, a headpiece 40, a flexible and positionable arm 50 and a laser emitter holder or handpiece 60. The device 20 may be mounted to or supported upon a shelf or surface 32 of the cart 30 during operation thereof. The cart 30 may include a height-adjustable column or vertical support 34, with a lower base 36 fitted with one or more wheels, casters, or other like structures. In particular, the laser device, system and method of the present invention represents a state of the art technology that allows the clinician to treat all body parts and conditions totally hands-fee and with little or no contact. For instance, in some embodiments, the laser device, system and method includes a 27.2 Watt (or other value, higher or lower) quad (or other) wavelength laser that provides doctors and patients hands-free treatment capabilities while allowing the doctor to see other patients at the same time. The laser device, system and method of at least one embodiment may be staff-driven and includes a plurality of (e.g., over a dozen) preset conditions. A quick three-touch sequence can activate the device and begin treatment.

FIGS. 2A-E illustrate various views of the cart or support structure 30, the components thereof, and basic assembly. For instance, the cart or support structure 30 of at least one embodiment is made of or includes components made of aluminum alloy. The height of the cart 30 is adjustable to provide optimal operator comfort. The cart 30 is stable with a large base including lockable casters for superior mobility. As shown in certain figures, the laser device 20 may be attached to or supported upon the cart 30, and in some cases, the cart 30 can be used as a charging station for the laser.

Figure 2A:
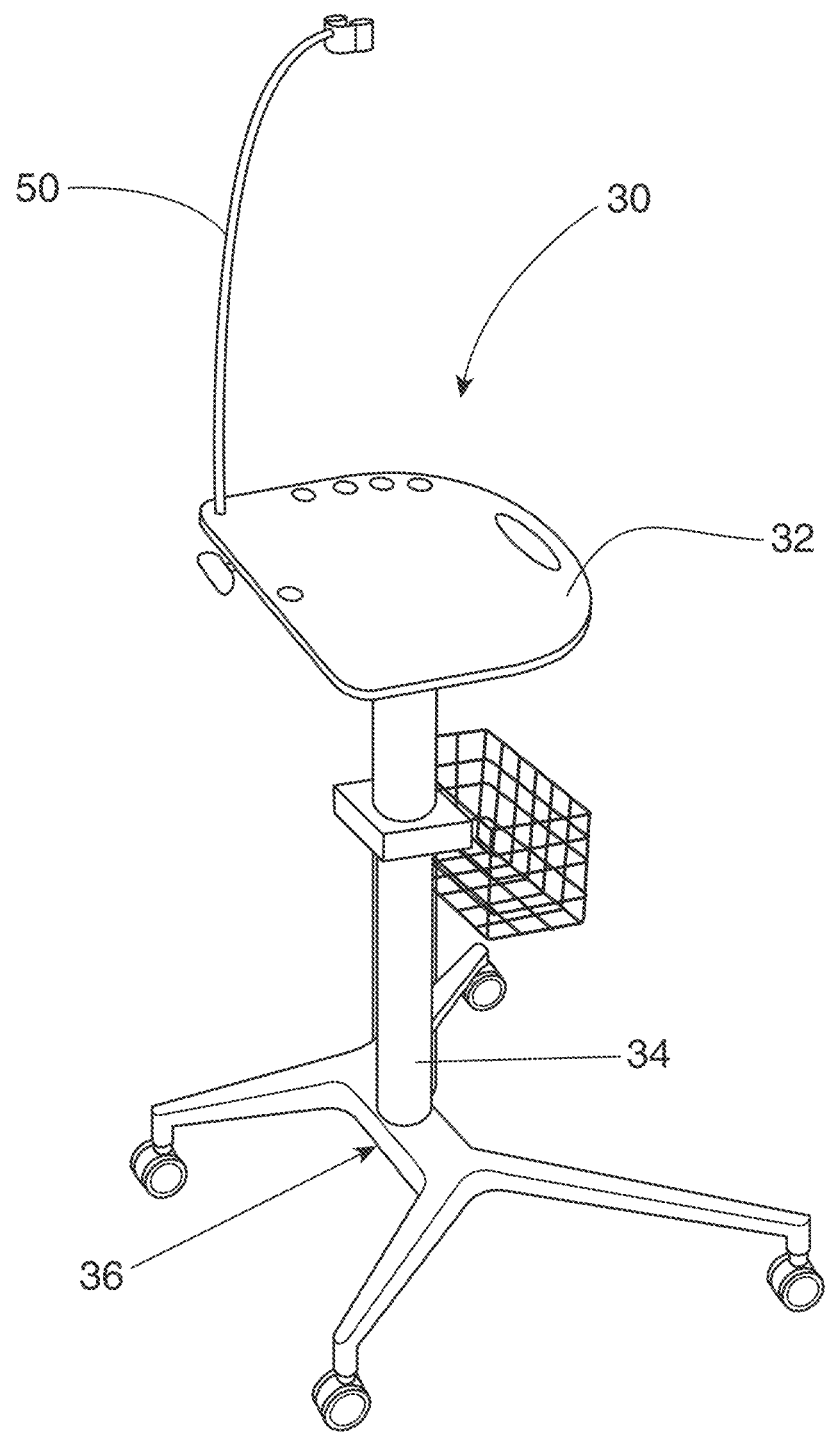
FIG. 2A is a perspective view of the cart and flexible arm as disclosed in accordance with at least one embodiment of the present invention.
Figure 2B:
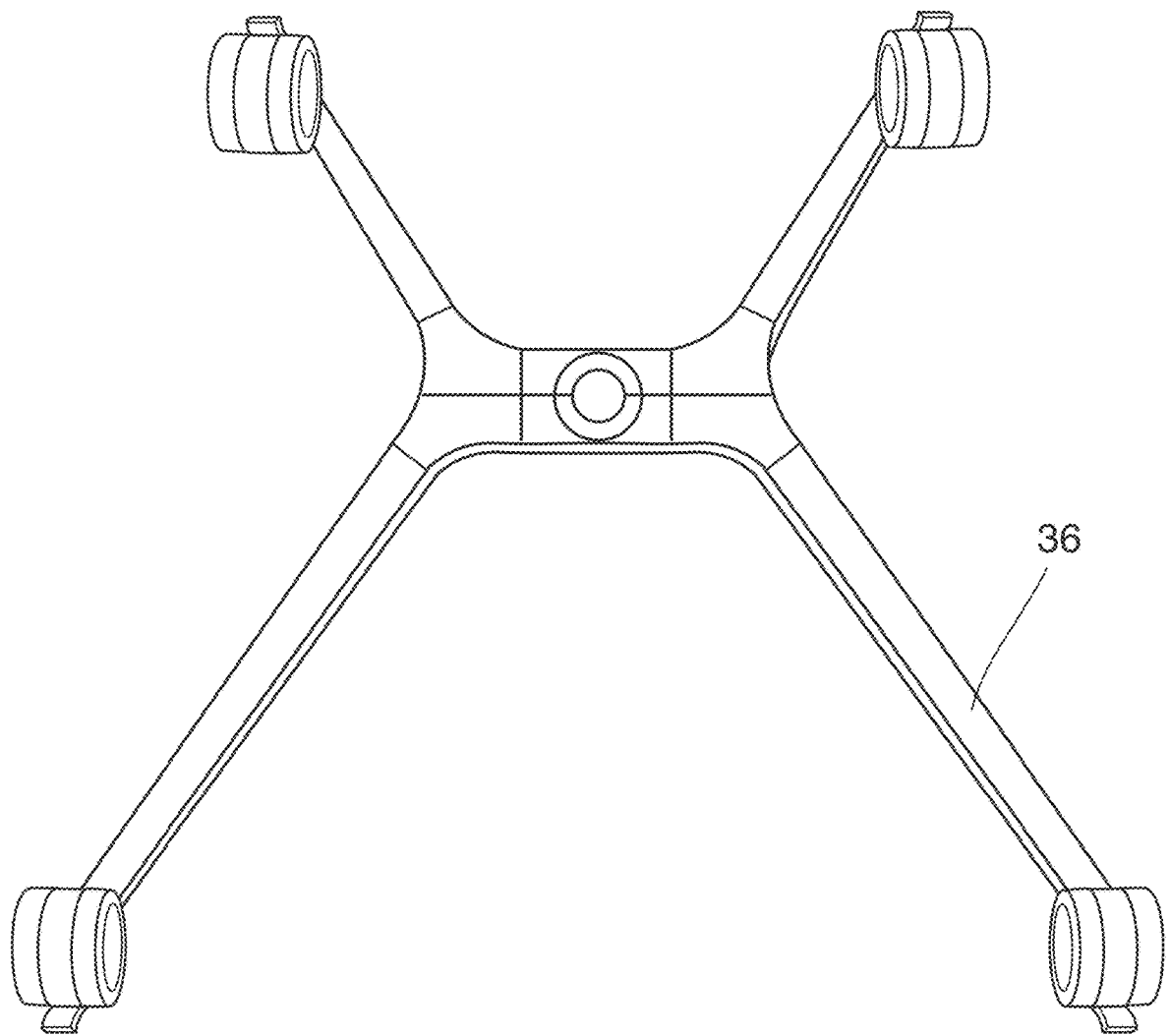
FIG. 2B is a bottom view of the cart as disclosed in accordance with at least one embodiment of the present invention.
Figure 2C:
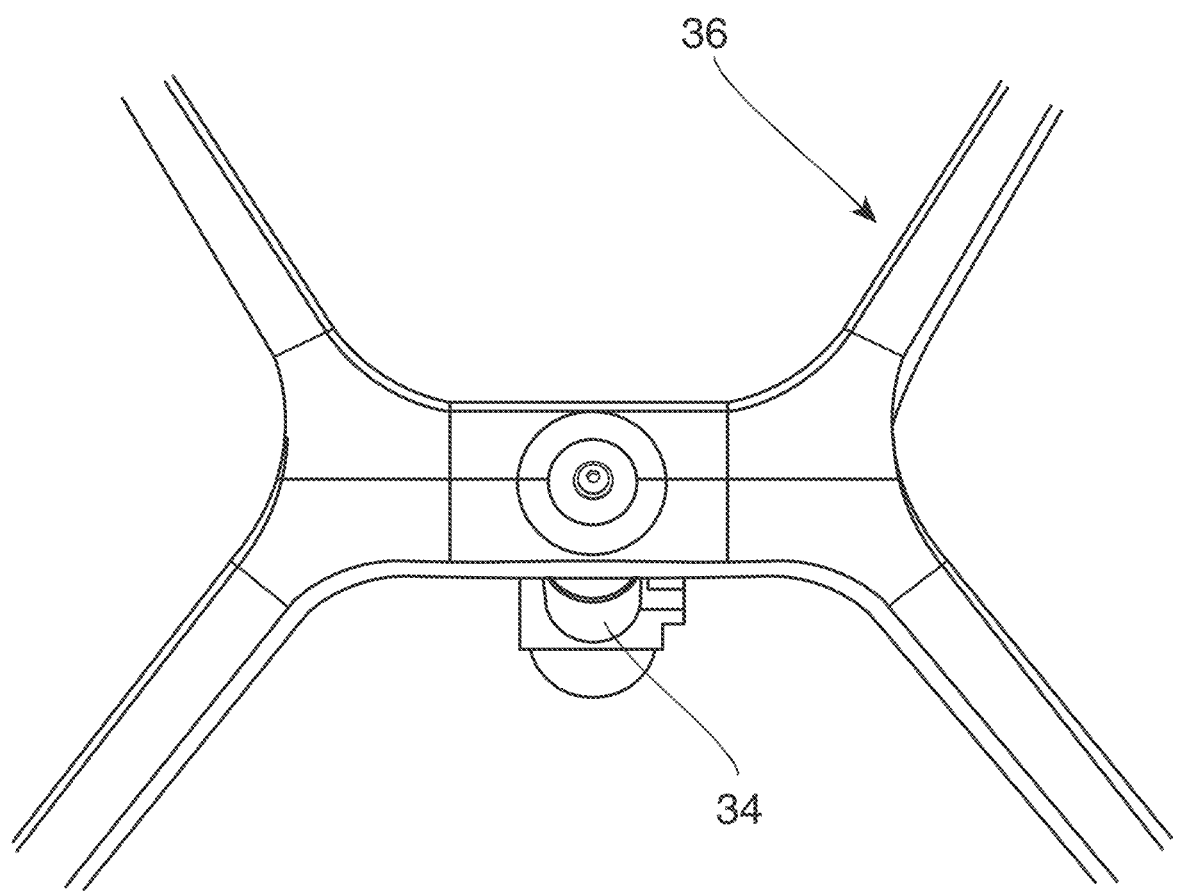
FIG. 2C is another bottom view of the cart as disclosed in accordance with at least one embodiment of the present invention.
Figure 2D:
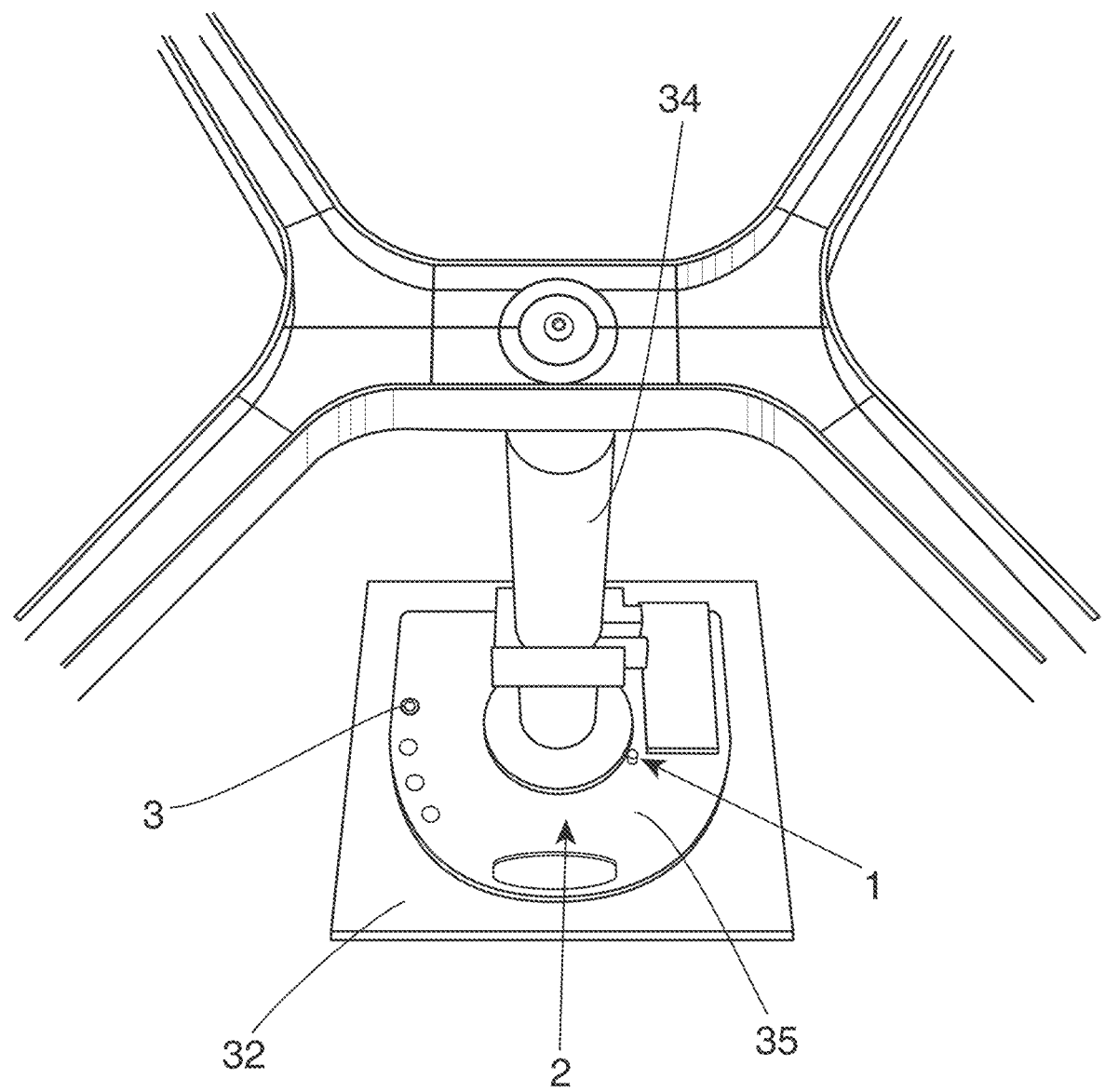
FIG. 2D is another bottom view of the cart as disclosed in accordance with at least one embodiment of the present invention.
Figure 2E:
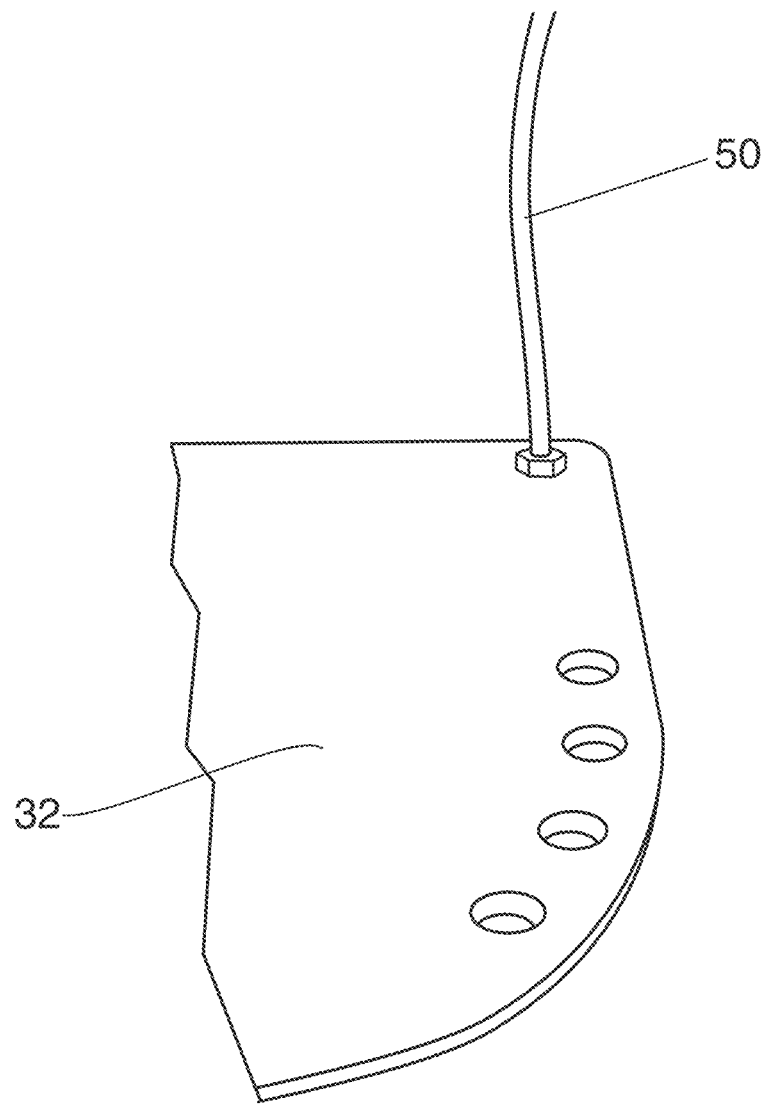
FIG. 2E is a partial view of the cart and flexible arm as disclosed in accordance with at least one embodiment of the present invention.

Furthermore, with reference to FIG. 2B, the cart 20 has four casters, at least one of which (and in the illustration two of which) are fitted with a brake. As shown in FIG. 2C, the base 36 is attached to the column 34 and fixed thereto with a screw or fastener. With reference to FIG. 2D, a connecting plate 35 is attached between the table 32 and the lifting lever. The table 32 is fixed with the lifting lever and the connecting plate via four screws or fasteners, and the lifting adjustment handle (used to adjust the height of table and length of the column) is fixed with three fasteners. As shown in FIG. 2E, the arm 50 of at least one embodiment may be fixed or attached to the cart or table 32 thereof via a nut secured on the bottom or undersurface of the table.

Moreover, the device 20 of at least one embodiment is structured and configured to generate certain laser outputs emitted through a laser wand or holder. The laser wand or holder may be attached to an end of the flexible arm 50 and/or to headpiece 40. In some embodiments, as illustrated, the flexible arm 50 may be attached, either removably or fixedly, to a portion of the cart 30. The arm 50 can be flexed or otherwise positioned into a desired orientation, angle, etc., e.g., adjacent, against or proximate to a body portion of the patient in order to deliver laser therapy thereto. As just an example, the laser therapy device 20 may be constructed and/or configured to deliver, generate or emit a laser various preset, programmed, programmable or selected wavelengths, including but in no way limited to 650 nanometers, 810 nanometers, 915 nanometers, and 980 nanometers. The device 20 or housing thereof may be lightweight (e.g., approximately 2.1 kilograms), compact with a module design, and may include one or more rechargeable internal or external batteries.

Figure 3A:
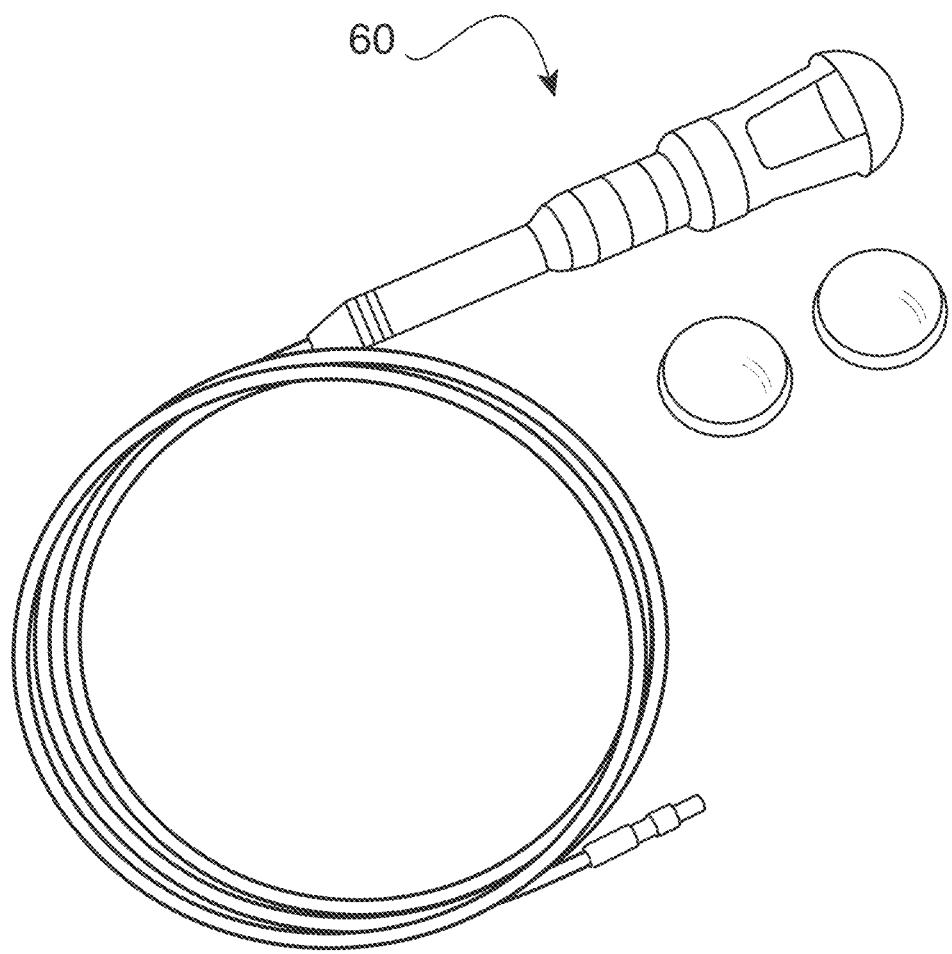
FIG. 3A is a to view of the laser emitter wand as disclosed in accordance with at least one embodiment of the present invention.
Figure 3B:
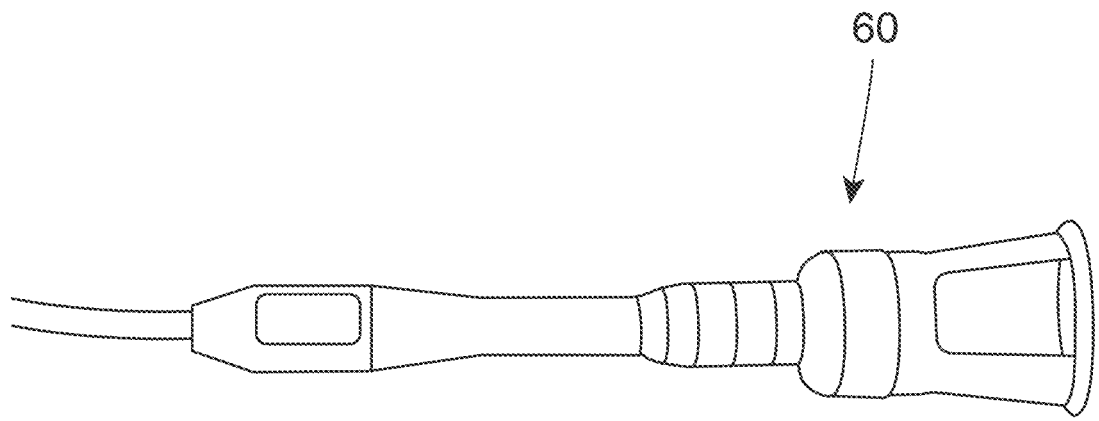
FIG. 3B is a partial view of the laser emitter wand as disclosed in accordance with at least one embodiment of the present invention.

FIGS. 3A-E illustrate some components of the system and method described herein. In particular, FIGS. 3A and 3B represent the laser emitter and/or laser emitter handpiece referenced as 60. The spot size may be adjustable or variable, for example, at 15 mm, 20 mm, 25 mm, and 30 mm, although other sizes are contemplated and within the scope of the present invention.

Figure 3C:
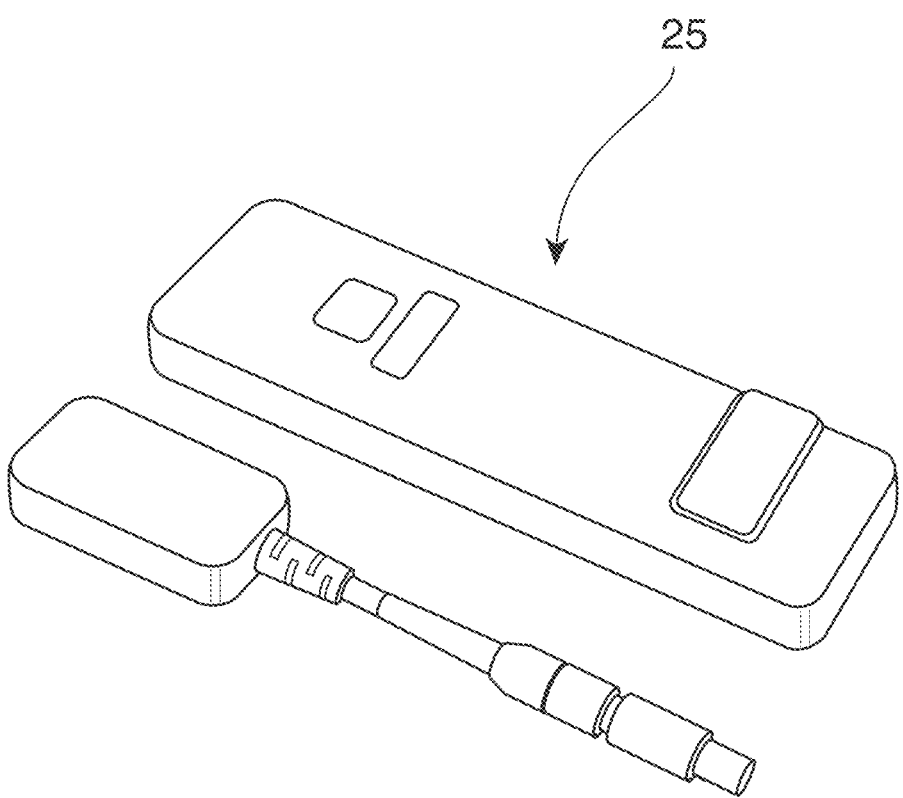
FIG. 3C is a perspective view of the start/stop switch as disclosed in accordance with at least one embodiment of the present invention.

FIG. 3C illustrates an exemplary unattended stop switch 25 allowing the patients to control the laser and in particular, to stop the laser if or when desired. In some cases, the switch 25 may be used to turn the laser on, turn the laser off, control the treatment time, etc. thereby making the process safe. The switch 25 may, therefore, the communicative with the laser device 20 and/or emitter 60, for example, via a wireless or wired connection. Further, the emitter shown in FIGS. 3A and 3B are illustrated before installation of the optical headpiece. In order to install the optical headpiece, portions of the emitted may be unscrewed or loosened and replaced with the optical headpiece.

Figure 3D:
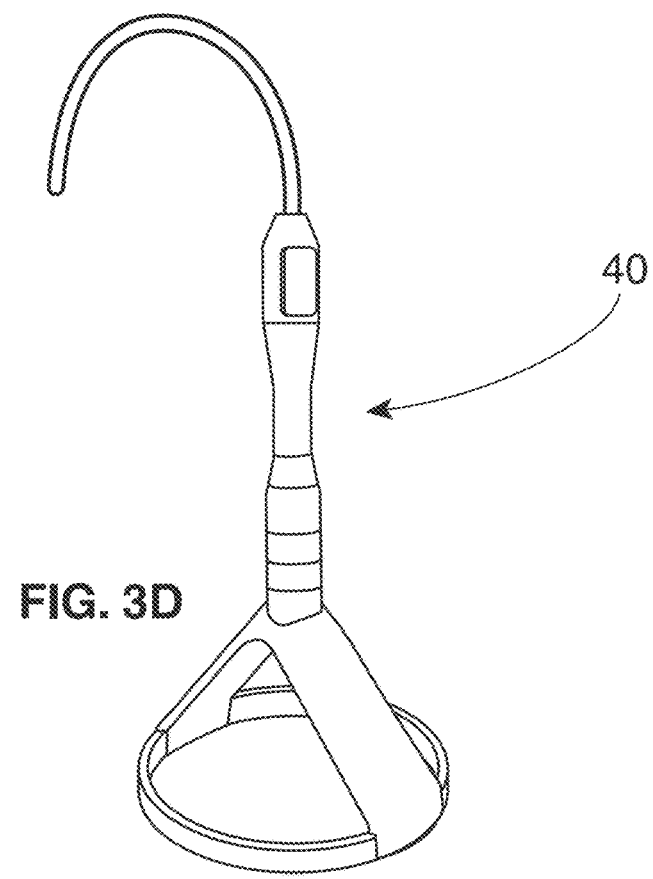
FIG. 3D is a side view of the optical headpiece as disclosed in accordance with at least one embodiment of the present invention.
Figure 3E:
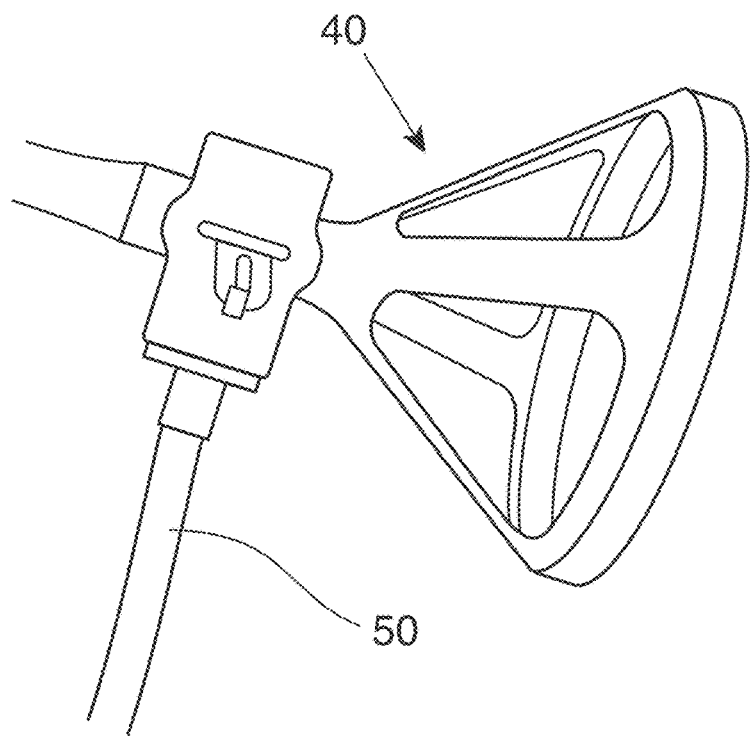
FIG. 3E is another side view of the optical headpiece as disclosed in accordance with at least one embodiment of the present invention.

FIGS. 3D-E represent an optic headpiece 40. In some cases, the headpiece 40 may be 100 mm in diameter, although other sizes are contemplated. It is designed to provide easier laser treatment on larger areas, and the special optics deliver energy uniformly across the entire treatment area and allow hands-free sessions without the risk of overheating.

Furthermore, the method at least one embodiment includes the following steps or processes.

Carefully unpack all of the components from the box or container.

Plug in the interlock into the back of the device.

Plug the power supply into the back of the laser. Make sure not to bend the small prongs on the plug in.

Plug the power supply into a grounded 110V wall outlet.

Turn on the laser (the on switch is on the back of the laser).

Figure 4:
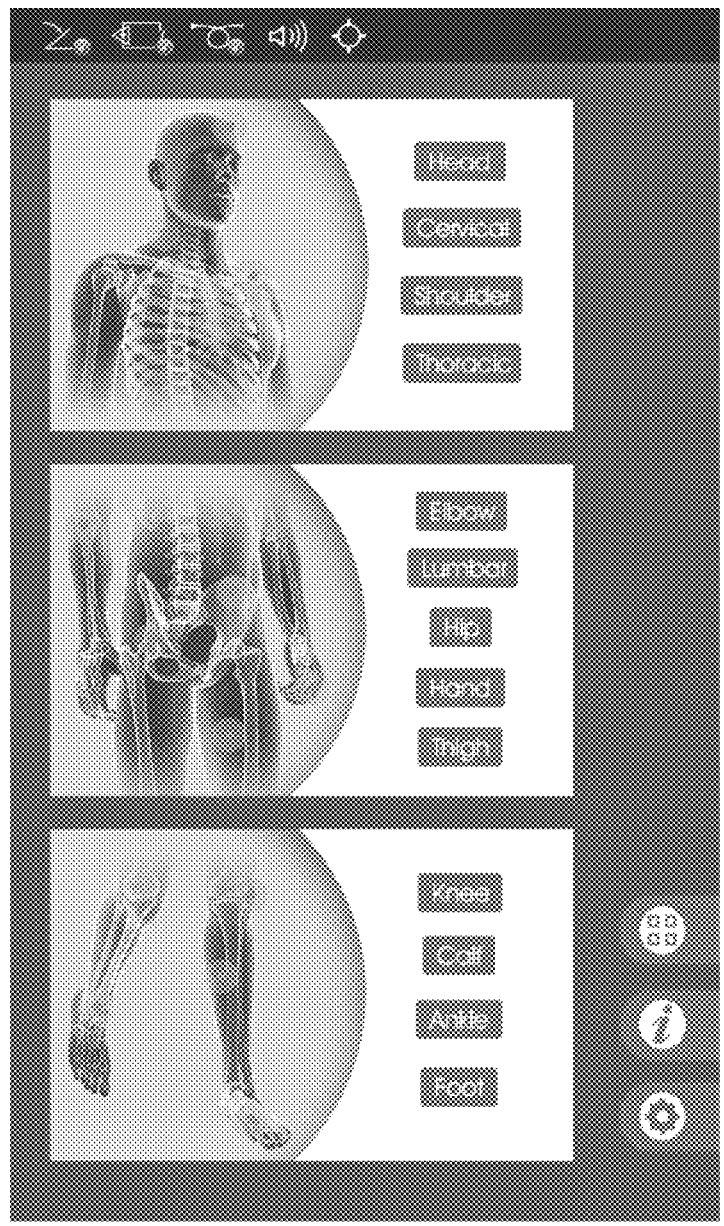
FIG. 4 is an exemplary screenshot of the laser treatment software component as disclosed in accordance with at least one embodiment of the present invention.

On the opening screen, enter the code or password (in some cases, the code or password may be a preprogrammed, four-digit code, such as but not limited to 0324, although other embodiments may have other passwords or codes). This will open the treatment screen 100 of at least one embodiment, for example, as shown in FIG. 4. In particular, FIG. 4 illustrates an exemplary screenshot of the treatment screen 100 which may be displayed on the device 20 of at least one embodiment of the present invention.

Next, select or press any body part or body portion from the treatment screen 100. For example, the treatment screen 100 displayed on the device 20 may show a plurality of different body parts or body portions, including, but in no way limited to: head, cervical, shoulder, thoracic, elbow, lumbar, hip, hand, thigh, knee, calf, ankle, foot. Other embodiments may include other body parts or body portions. The device 20 of at least one embodiment is programmed with treatment settings associated with each of the different selectable body parts or portions. Selecting one of the body parts or portions will therefore automatically set up the treatment based upon the preprogrammed treatment settings associated with the selected body part or portion.

In at least one embodiment, the user may not edit the treatment settings or parameters that are preprogrammed for the hands-free operation mode. These settings were designed for maximum patient comfort and response. More in particular, the treatment settings of at least one embodiment associated with each of the different body parts or portions have been configured for maximum power, the correct Joules of therapeutic energy and the best or optimum scenario to avoid thermal overload of the patient's skin. This removes, eliminates or reduces the "doctor error" factor by stopping the therapist from using too much power, too little power, or wrong treatment times. In other words, in some embodiments, the preprogrammed or preset treatment settings or protocols may include a particular amount of power or a range of power, a pulse range, and a time of treatment that covers all bases.

It should be noted that in some embodiments, the treatment settings or protocols may be different for different body parts or portions. For example, the treatment settings or protocols (e.g., power, heat, power range, pulse range, time of treatment, etc.) for the ankle may be different than the treatment settings or protocols for the thigh.

As mentioned above, in at least one embodiment, the treatment settings or parameters that are preprogrammed for the hands-free operation mode are fixed or are otherwise not adjustable, and therefore may not be changed by the user or doctor. In some embodiments, however, the user or doctor may be able to lower at least some of the settings, such that the preprogrammed treatment settings or protocols may be considered a maximum level. In this manner, the user or doctor may, in some cases, lower the power or joules, lower the pulse range, lower the time of treatment, etc. from the preprogrammed treatment settings or protocols. In yet another embodiment, it is contemplated that the preprogrammed treatment settings or protocols (e.g., power, heat, power or pulse range, time, etc.) may be altered by being raised or lowered by the doctor or user.

Next, make sure the optical headpiece 40 is attached to the emitter body. In many cases it is not advisable to treat hands free without an optical headpiece 40, and in some cases, never treat hands free with anything other than the round optical headpiece 40.

After inserting the emitter into the flex arm emitter holder, move the flex arm 50 and position the optical headpiece 40 on, against, or close to the body part or portion previously selected, for example, on the treatment screen 100. For instance, once the flex arm 50 is securely mounted to the table top 32, the flex arm 50 can be moved and shaped to fit the patient's needs. When not in use, the flex arm 50 may be positioned straight up or substantially upward and out of the way. The flex arm 50 is sturdy and will hold the emitter and optical headpiece in place without movement. Some embodiments of the present invention allow the optical headpiece 40 to be placed against the area being treated. In some cases, positioning the headpiece 40 approximately one inch from the surface of the skin work well, although other distances are contemplated and other distances may be more ideal for different patients, skin tone or color, skin conditions, etc.

Make sure everyone present is wearing protective eyewear.

Press "standby" or other similar activation button.

In some embodiments a start/stop switch 25 (e.g., a wireless or wired switch) may be used to activate and/or deactivate the laser, for example, by pressing a "start" button or its equivalent and/or by pressing a "stop" button or its equivalent.

Once the laser is activated, or in some cases before the laser is activated, the stop switch 25 may be provided to the patient. In such a case, the patient may use the stop switch 25 (e.g., by activating or pressing a button or switch thereon) to stop treatment and/or otherwise stop the laser at any time. If a patient complains that the treatment is too warm, the optical headpiece 40 may be moved further from the patient's skin. Patients with darker skin or with tattoos on or near the treatment area of the skin may require the optical headpiece 40 or laser to be moved one inch or more from the skin, for instance, due to the ink and/or difference in melatonin. Moving the optical headpiece 40 and/or laser one to two inches from the skin surface will not adversely affect treatment.

If a patient continually complains about thermal build-up or any other issue, the treatment should be stopped immediately.

When the treatment is finished, the device may sound a report and/or emit an audible notification. In order to return to the programming or treatment screen 100, the user may select a button (e.g., the bottom wheel button). This will take the software to the device setting screen. The user may then press "switching system" to go back to the code entry screen. The user can then press or enter a code (e.g., 1234) to go to attended therapy.

FIGS. 5A-D demonstrate the application of the hands-free therapy system of at least one embodiment of the present invention. In FIGS. 5A-D, the optical headpiece 40 has been placed directly on the area of treatment. The patient is wearing safety glasses and has the remote switch 25 in hand to selectively stop treatment at any desired time.

Figure 5A:
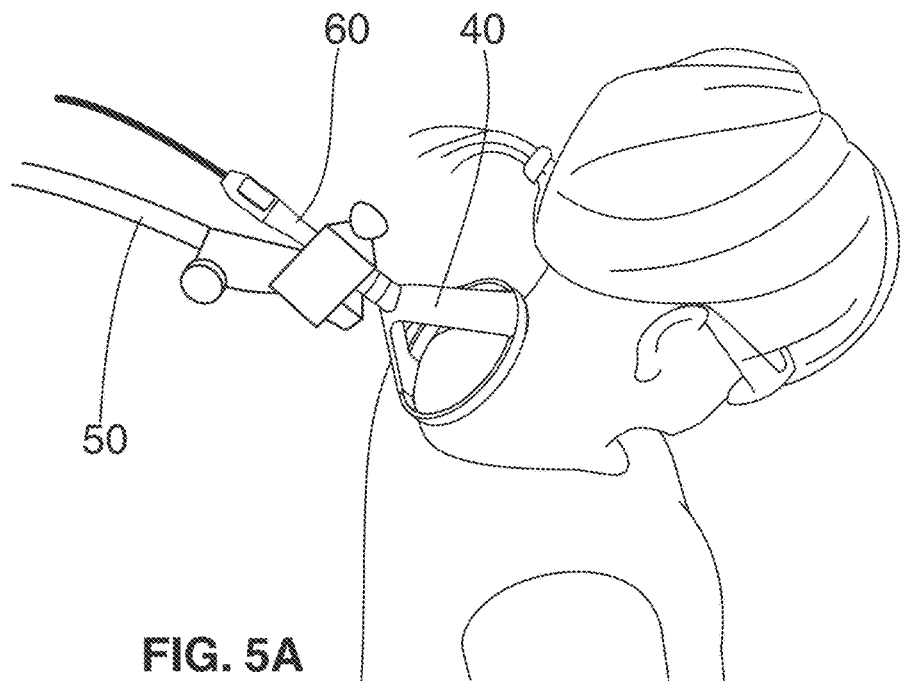
FIGS. 5A through 5E are exemplary photographs of hands-free laser treatment using the device, system and method as disclosed in accordance with at least one embodiment of the present invention.
Figure 5B:
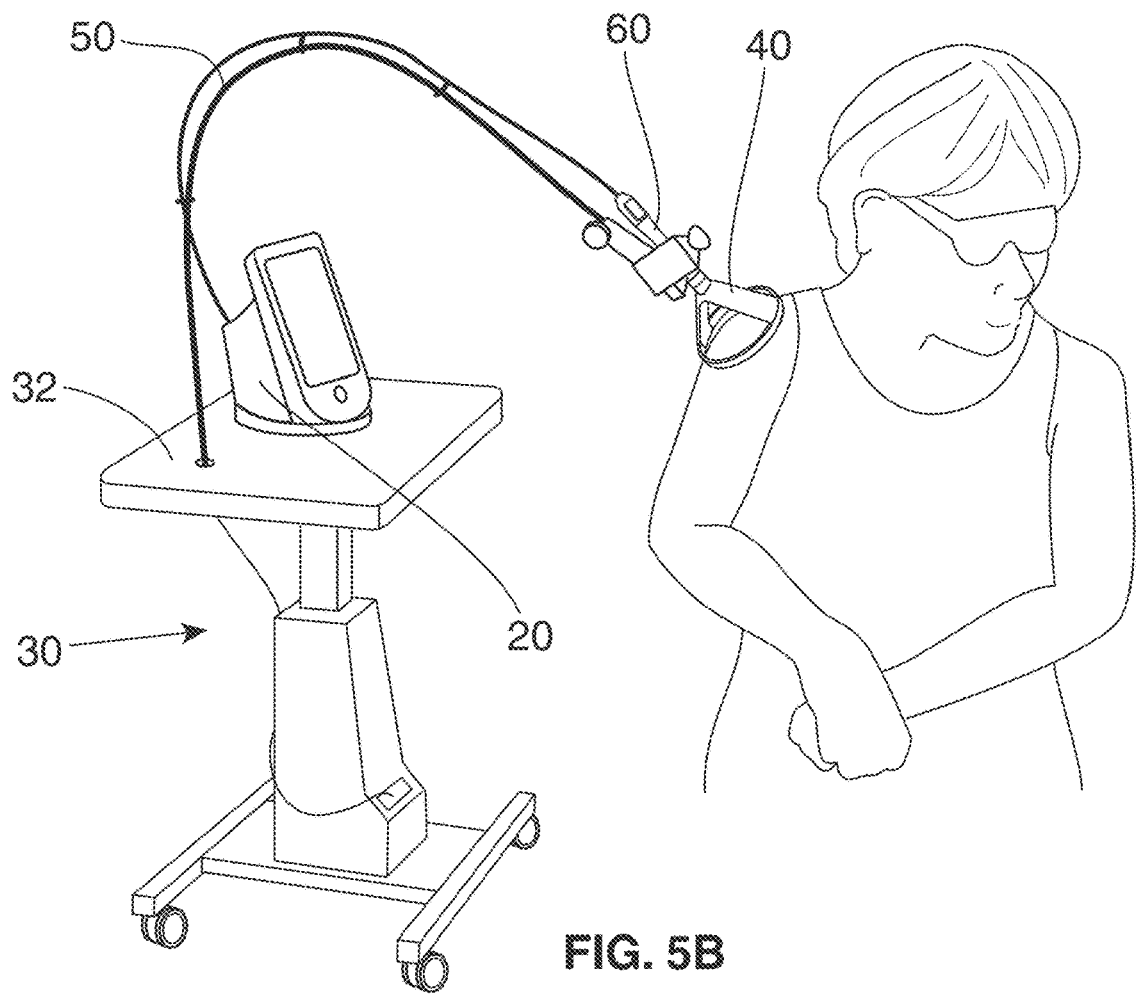
Figure 5C:
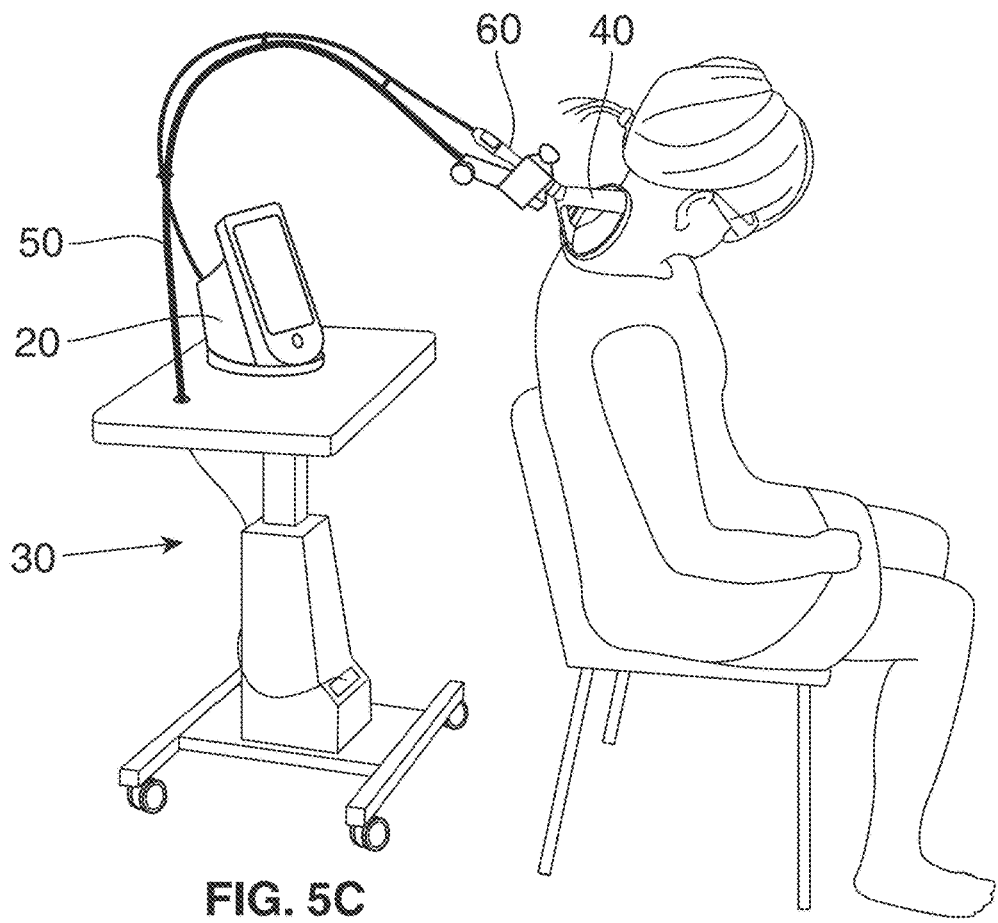
Figure 5D:
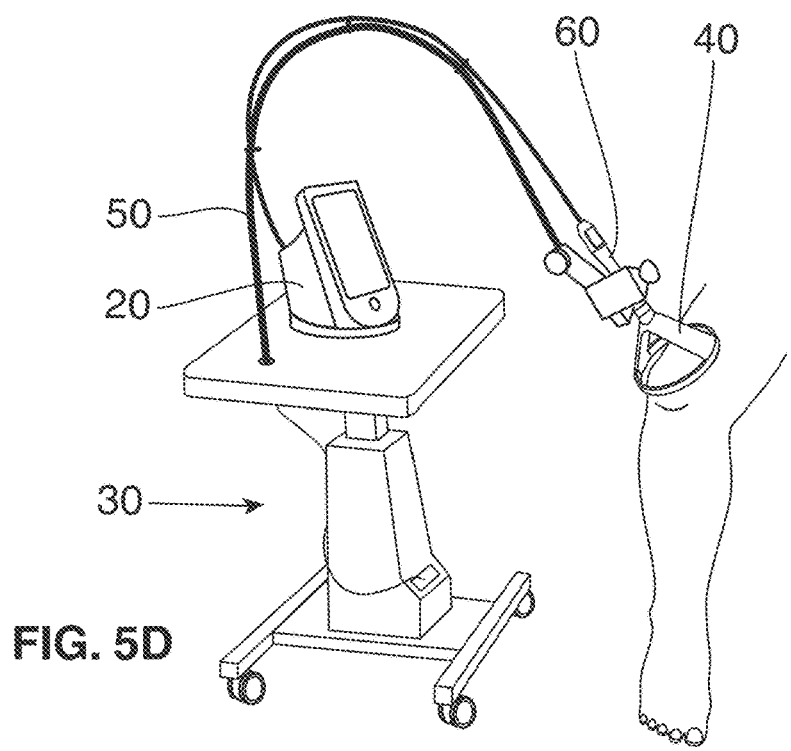
Figure 5E:
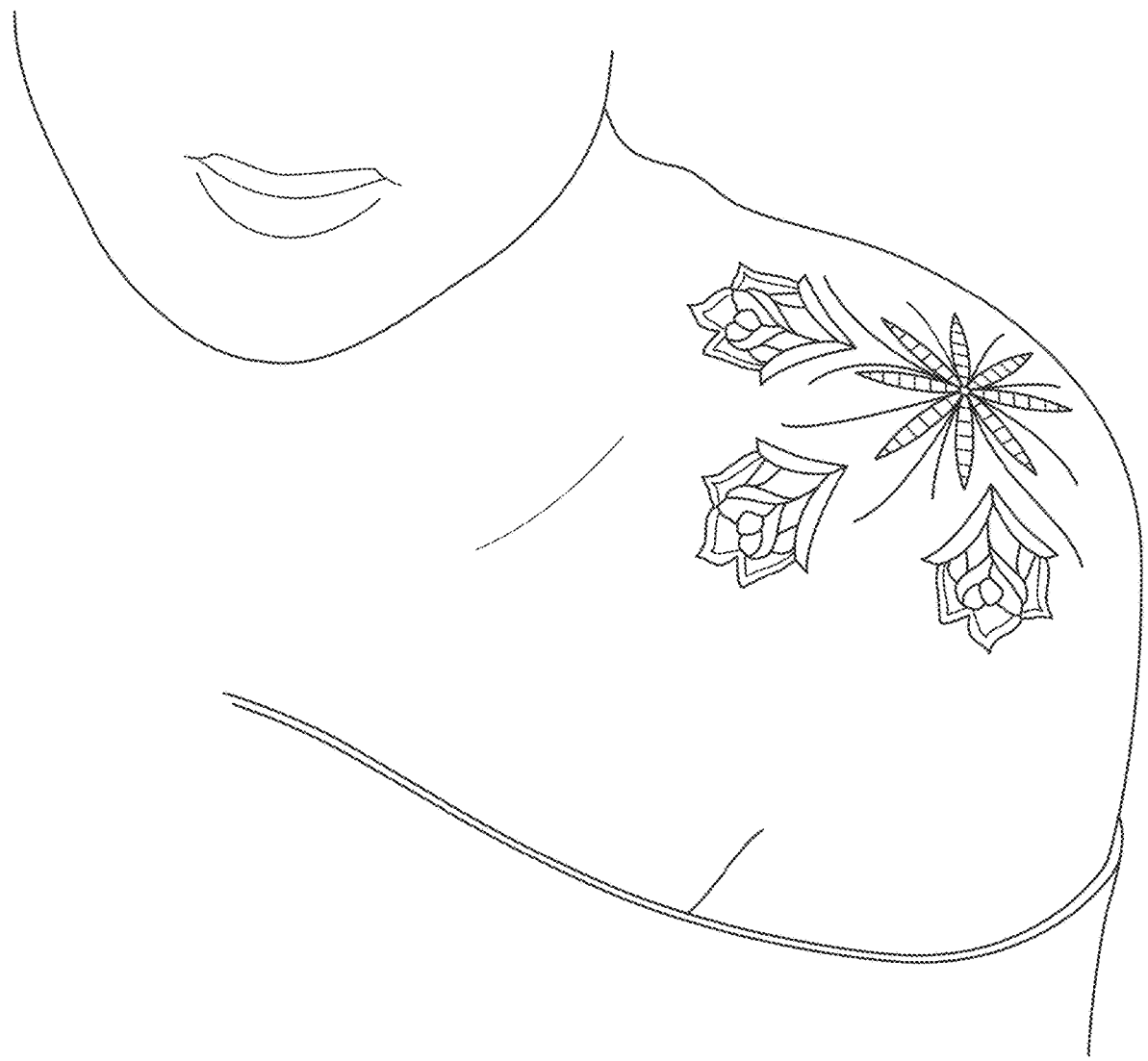
Figure 6C:
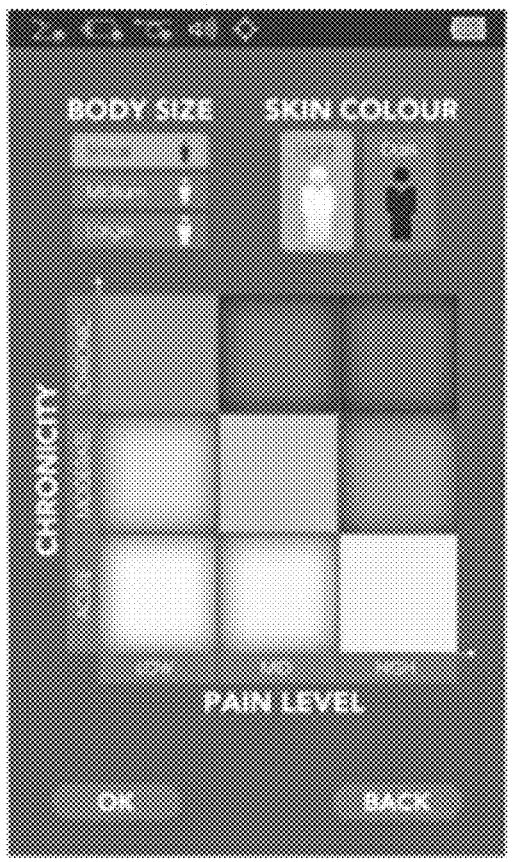
FIG. 6A though 6F are additional exemplary screenshots of the laser treatment software component as disclosed in accordance with at least one embodiment of the present invention.
Figure 6D:
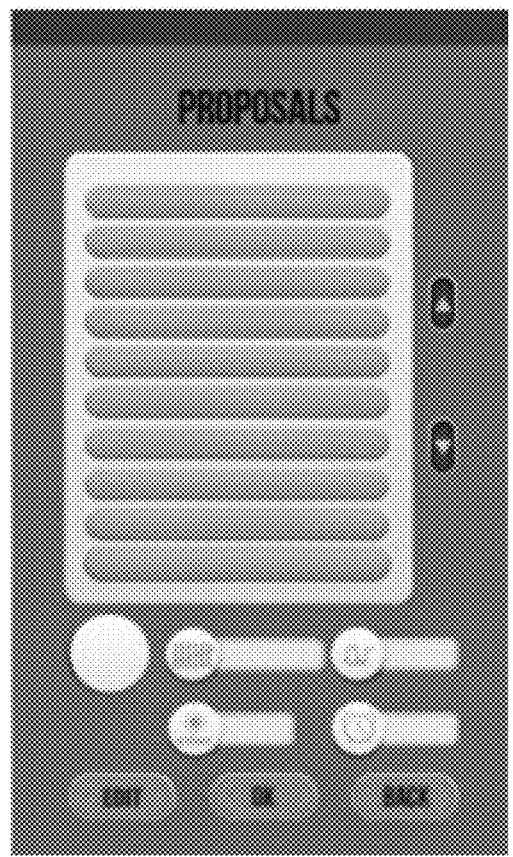
Figure 6E:
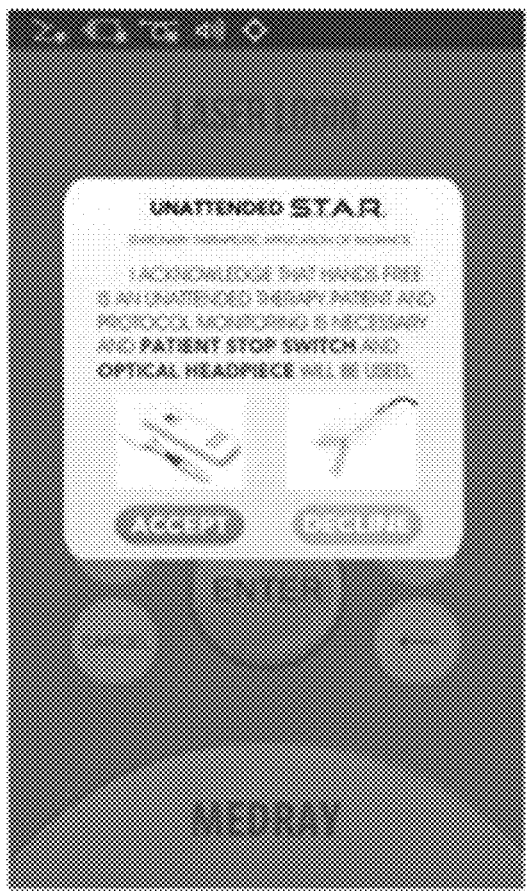
Figure 6F:
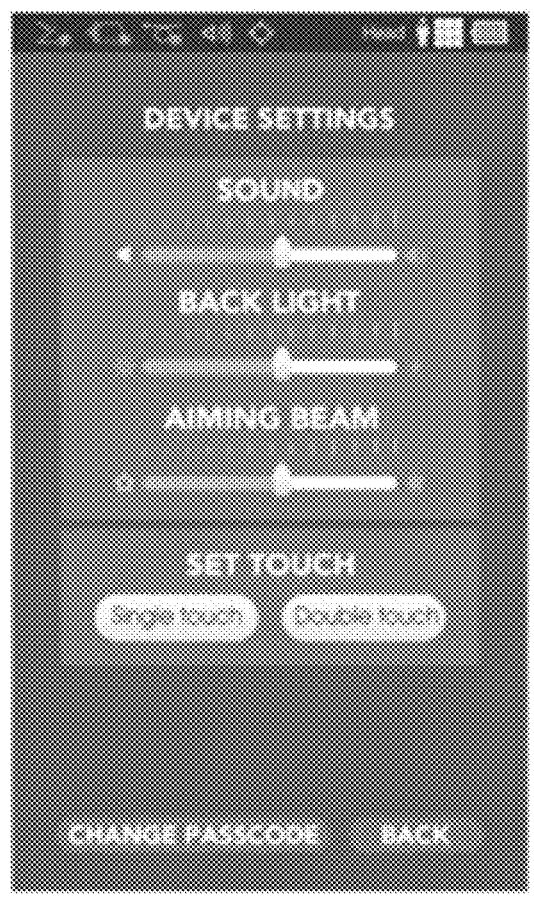

With reference to FIG. 5E, it should be noted that on tattoos or patients with darker skin, the system and method may operate best with the optical headpiece 40 moved off of, or further away from the skin. Tattoos and dark skin absorb the laser treatment much easier because of altered melatonin. The first time a patient with a tattoo on or near the treatment area or a patient with dark skin is treated, the patient should be monitored for pain, too much warmth, or thermal overload. The optical headpiece 40 may be moved one inch or more off of the skin surface. The therapeutic affect will not be altered in any significant manner by doing so. In addition, a small fan may be used to blow air on the skin surface during treatment, particularly for patients with extensive tattoos, ink or dark skin at the treatment area.

Additional features of certain embodiments of the device, system and method of the present invention may include the ability to make and save personalized treatments, adjust treatment protocols for different body parts or portions, perform attended treatments, periodic software and/or hardware upgrades, etc.

FIGS. 6A-F illustrate additional screenshots 202, 204, 206, 208, 210, 212 of the device or software used in connection with at least one embodiment of the present invention. In particular, the lasers and devices of certain embodiments may be developed with a plurality (e.g., hundreds) of built-in therapy protocols and powerful functions that users can effortlessly perform various types of treatments and settings in a few clicks. The user interface is easy and clear that can guide doctors or other users to operate various therapy treatments and settings step by step on a high resolution touch screen.

Class IV therapy lasers of single wavelength, dual wavelength, quad wavelengths, etc. provide high flexibility and high fitness for different clinical conditions.

Unattended mode allows patients to control laser light and treatment processes via a wireless (or wired) hand switch, so everything is under control even when the doctor is not around or present during treatment.

With reference to FIG. 7, the treatment settings and protocols of at least one exemplary embodiment of the present invention are illustrated, for example, with reference to 300. These settings and protocols (e.g., light skin CW power, light skin CW phase time, light skin pulsing average power, light skin pulsing phase time, part size, size and multiplier) for each body part, location or portion (e.g., ankle, calf, cervical, elbow, foot, head, hand, hip, jaw, knee, lumbar, sacrum, shoulder, thigh, thoracic, wrist, etc.) have been configured for maximum power, the correct joules of therapeutic energy and the best scenario to avoid or minimize thermal overload of the skin. The settings and protocols illustrated in FIG. 7 should be considered exemplary in nature and may be different for different embodiments. In addition, the settings and protocols may be adjusted based on acute or chronic selections, part size, skin color, pain level, etc.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention. This written description provides an illustrative explanation and/or account of the present invention. It may be possible to deliver equivalent benefits using variations of the specific embodiments, without departing from the inventive concept. This description and these drawings, therefore, are to be regarded as illustrative and not restrictive.

The invention claimed is:

1. A laser therapy system, comprising:
a support assembly,
a laser treatment device supported upon a portion of said support assembly,
said laser treatment device being configured to provide hands-free laser treatment, wherein said laser treatment device comprises a laser treatment software component installed thereon,
said laser treatment software component comprising a plurality of preprogrammed treatment protocols, wherein each of said plurality of preprogrammed treatment protocols are associated with at least one of a plurality of body locations, wherein each of said plurality of preprogrammed treatment protocols comprises a predetermined laser treatment level and a predetermined time of treatment,
wherein, upon selection of one of said plurality of body locations via said laser treatment software component on said laser treatment device, said laser emitter is configured to emit laser treatment according to a corresponding one of said preprogrammed plurality of treatment protocols for hands-free unattended laser treatment.

2. The system as recited in claim 1 further comprising a positionable arm with a first end and a second end, wherein said first end of said positionable arm is mounted to said support assembly.

3. The system as recited in claim 2 further comprising a laser emitter secured to said second end of said positionable arm.

4. The system as recited in claim 3 further comprising an optical headpiece is mounted to said second end of said positionable arm.

5. The system as recited in claim 1 wherein said support assembly comprises a cart with a base, a height-adjustable column and a tabletop.

6. The system as recited in claim 5 wherein said laser treatment device is support upon said tabletop of said cart.

7. The system as recited in claim 6 wherein said optical headpiece at least partially surrounds said laser emitter.

8. The system as recited in claim 7 wherein said optical headpiece comprises a round outer edge, wherein said round edge is in contact with or spaced from a surface of a patient's skin during the unattended laser therapy treatment.

9. The system as recited in claim 1 wherein the body locations comprises at least one upper body location, at least one middle body location and at least one lower body location.

10. The system as recited in claim 9 wherein said at least one upper body location comprises at least one of: a head, a cervical, a shoulder, and a thoracic.

11. The system as recited in claim 9 wherein said at least one middle body location comprises at least one of: an elbow, a lumbar, a hip, a hand, and a thigh.

12. The system as recited in claim 9 wherein said at least one lower body location comprises at least one of: a knee, a calf, an ankle and a foot.

13. The system as recited in claim 9 wherein each of said plurality of body locations comprises one of said preprogrammed plurality of treatment protocols defining at least a laser treatment level and a time of treatment.

14. The system as recited in claim 13 wherein each of said preprogrammed plurality of treatment protocols are fixed and not adjustable.

15. The system as recited in claim 13 wherein said laser treatment level and said time of treatment associated with each of said preprogrammed plurality of treatment protocols are fixed.

16. A laser therapy system for laser therapy treatment, said system comprising:
 a support assembly, and
 a laser treatment device supported upon said support assembly,
 wherein said laser treatment device comprises a plurality of preprogrammed treatment protocols,
 wherein each of said plurality of preprogrammed treatment protocols are associated with at least one of a plurality of body locations,
 wherein each of said plurality of preprogrammed treatment protocols comprises a predetermined laser treatment level and predetermined time of treatment,
 wherein, upon selection of one of said plurality of body locations on said laser treatment device, a laser emitter is configured to emit laser treatment according to a corresponding one of said preprogrammed plurality of treatment protocols for hands-free unattended laser treatment.

17. The system as recited in claim 16 further comprising a stop switch communicative with said laser treatment device, wherein said stop switch is configured to selectively stop the laser therapy treatment at the option of a patient.

18. The system as recited in claim 16 further comprising a flexible and positionable arm comprising a first end and a second end, wherein said first end of said flexible and positionable arm is mounted to said support assembly, and said laser emitter is secured to said second end of said flexible and positionable arm.

19. The system as recited in claim 18 further comprising an optical headpiece mounted to said second end of said flexible and positionable arm in an at least partially surrounding relation to said laser emitter.

20. A laser therapy system, comprising:
 a support assembly,
 a laser treatment device supported upon a portion of said support assembly and comprising a laser treatment software component,
 said laser treatment software component comprising a plurality of preprogrammed treatment protocols, wherein each of said plurality of preprogrammed treatment protocols are associated with at least one of a plurality of body locations, wherein each of said plurality of preprogrammed treatment protocols comprises a predetermined laser treatment level and a predetermined time of treatment,
 wherein the body locations comprises at least one upper body location, at least one middle body location and at least one lower body location,
 wherein said at least one upper body location comprises at least one of: a head, a cervical, a shoulder, and a thoracic,
 wherein said at least one middle body location comprises at least one of: an elbow, a lumbar, a hip, a hand, and a thigh,
 a positionable arm mounted to said support assembly,
 a laser emitter secured to an end of said positionable arm, and
 wherein, upon selection of one of said plurality of body locations via said laser treatment software component on said laser treatment device, said laser emitter is configured to emit laser treatment according to a corresponding one of said preprogrammed plurality of treatment protocols for hands-free laser treatment.

* * * * *